United States Patent [19]
Sperl et al.

[11] Patent Number: 6,066,634
[45] Date of Patent: *May 23, 2000

[54] SUBSTITUTED CONDENSATION PRODUCTS OF N-BENZYL-3-INDENYLACETAMIDES HETEROCYCLIC ALDEHYDES FOR NEOPLASIA

[75] Inventors: Gerhard J. Sperl, North Wales, Pa.; Paul Gross, Stockton, Calif.; Klaus Brendel, Tuscon, Ariz.; Gary A. Piazza, Doylestown; Rifat Pamukcu, Spring House, both of Pa.

[73] Assignees: Cell Pathways, Inc., Horsham, Pa.; University of Arizona, Tuscon, Ariz.

[*] Notice: This patent is subject to a terminal disclaimer.

[21] Appl. No.: 09/206,245

[22] Filed: Dec. 7, 1998

Related U.S. Application Data

[63] Continuation-in-part of application No. 08/989,353, Dec. 12, 1997.

[51] Int. Cl.[7] .......................... A61K 31/34; A61K 31/38; A61K 31/4409; A61K 31/47; C07D 213/56

[52] U.S. Cl. .......................... 514/241; 514/255; 514/256; 514/307; 514/311; 514/357; 514/365; 514/381; 514/394; 514/400; 514/406; 514/419; 514/427; 514/461; 546/333

[58] Field of Search .................... 514/241, 256, 514/311, 365, 394, 406, 427, 255, 307, 357, 381, 400, 419, 461; 546/333

[56] References Cited

PUBLICATIONS

Izzo et al., Medline Abstract No. 98349734, 1998.

Christensen et al., Isozyme–Selective Phosphodiesterase Inhibitors as Antiasthmatic Agents, Annual Reports in Medicinal Chemistry, vol. 29, pp. 185–194, 1994.

Thompson et al., Assay of Cyclic Nucleotide Phosphodiesterase and Resolution of Multiple Molecular Forms of the Enzyme, Advances in Cyclic Nucleotide Research, vol. 10, pp. 69–92, 1979.

*Primary Examiner*—Mukund J. Shah
*Assistant Examiner*—Deepak R. Rao
*Attorney, Agent, or Firm*—Robert W. Stevenson

[57] ABSTRACT

Substituted condensation products of N-benzyl-3-indenylacetamides with heterocyclic aldehydes are useful for inducing or promoting apotosis and for arresting uncontrolled neoplastic cell proliferation, and are specifically useful in the arresting and treatment of neoplasias, including precancerous and cancerous lesions.

28 Claims, No Drawings

SUBSTITUTED CONDENSATION PRODUCTS OF N-BENZYL-3-INDENYLACETAMIDES HETEROCYCLIC ALDEHYDES FOR NEOPLASIA

This application is a continuation-in-part of U.S. application Ser. No. 08/989,353 filed Dec. 12, 1997.

TECHNICAL FIELD

This invention relates to compounds and methods for inducing or promoting apotosis and for arresting uncontrolled neoplastic cell proliferation, methods that are specifically useful in the arresting and treatment of neoplasias, including precancerous and cancerous lesions.

BACKGROUND OF THE INVENTION

Pharmaceuticals that are effective against early stage neoplasias comprise an emerging and expanding area of research and potential commercial development. Such pharmaceuticals can delay or arrest development of precancerous lesions into cancers. Each year in the United States alone, untold numbers of people develop precancerous lesions, which exhibit a strong statistically significant tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), cervical dysplasia (cervical cancer) and other such neoplasms.

Compounds that prevent or induce the remission of existing precancerous or cancerous lesions, or carcinomas, delay the onset of cancer and would greatly reduce illness and death from at least certain forms of that disease.

Such compounds and methods are particularly beneficial to sub-populations of patients who repeatedly develop precancerous lesions, and therefore have a statistically higher probability of getting cancer. Many cancer types (e.g., breast, colon, prostate etc.) have such patient sub-populations. One example of a sub-population that will invariably develop cancer (if left untreated) includes those patients who suffer from familial polyposis of the colon. Familial polyposis patients typically develop many (e.g., hundreds or thousands) of colonic polyps beginning in their teenage years. Because each colonic polyp (whether familial or non-familial) reportedly has approximately a five percent lifetime risk of developing into a cancer, the treatment of choice—until very recently—for familial polyposis patients is surgical removal of the colon in the early twenties.

Many other cancers have sub-populations that also have much higher risks for getting cancer at an early age and for having the cancer reoccur, than patients as a whole who get such a cancer. For example, such sub-populations have been identified among breast cancer patients and colon cancer patients. In the latter sub-population, removal of the individual polyps as they form is the current treatment of choice. Removal of polyps in non-familial patients has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation.

The search for drugs useful for treating and preventing neoplasias in their earliest stages is intensive because chemotherapy and surgery on cancer itself is often not effective, and current chemotherapy has severe side effects. Thus, the search for compounds effective against precancerous lesions without the side effects of conventional chemotherapy is particularly intensive. Such compounds are also envisaged for recovered cancer patients who retain a risk of cancer reoccurrence, and even for cancer patients who would benefit from compounds that selectively induce apoptosis in neoplastic, but substantially not in normal cells.

Standard cancer chemotherapeutic drugs are not considered appropriate drugs for cancer chemoprevention because whatever cancer preventative (as opposed to cancer-fighting) capabilities those drugs may possess do not outweigh their severe side effects. Most standard chemotherapeutics are now believed to kill cancer cells by inducing apoptosis (also sometimes referred to as "programmed cell death"). Apoptosis naturally occurs in virtually all tissues of the body. Apoptosis plays a critical role in tissue homeostasis, that is, it ensures that the number of new cells produced are correspondingly offset by an equal number of cells that die. Apoptosis is especially pronounced in self-renewing tissues such as bone marrow, immune cells, gut, and skin. For example, the cells in the intestinal lining divide so rapidly that the body must eliminate cells after only three days to protect and prevent the overgrowth of the intestinal lining.

Standard chemotherapeutics promote apoptosis not only in cancer cells, but also in normal human tissues, and therefore have a particularly severe effect on cells that normally divide rapidly in the body (e.g. hair, gut and skin). The results of those effects on normal cells include hair loss, weight loss, vomiting and bone marrow immune suppression. This is one reason standard chemotherapeutics are inappropriate for cancer prevention.

In the absence of a one-time cure (e.g., a gene therapy), another reason is that cancer prevention therapy requires chronic administration of a pharmaceutical to repress neoplasia formation, which for standard chemotherapeutics is obviously contraindicated because of the types of side effects discussed above.

Abnormalities in apoptosis can lead to the formation of precancerous lesions and carcinomas. Also, recent research indicates that defects in apoptosis play a major role in other diseases in addition to cancer. Consequently, compounds that modulate apoptosis could be used in the prevention or control of cancer, as well as other diseases.

Several non-steroidal anti-inflammatory drugs ("NSAIDs"), originally developed to treat arthritis, have shown effectiveness in inhibiting and eliminating colonic polyps. Polyps virtually disappear when the patients take the drug, particularly when the NSAID sulindac is administered. However, the continued prophylactic use of currently available NSAIDs, even in polyposis syndrome patients, is still marked by severe side reactions that include gastrointestinal irritations, perforations, ulcerations and kidney toxicity believed to be produced by inhibition of prostaglandin synthetase activity ("PGE-2"). Such inhibition is a requirement for the NSAIDs anti-inflammatory action since elevated levels of PGE-2 are associated with inflammation. PGE-2 plays a protective function in the gastrointestinal tract, which is the reason such gastric side effects arise with chronic NSAID therapy, which is rarely indicated for arthritis sufferers, acute therapy being the norm for them. However, chronic administration of sulindac is important for polyposis patients to eliminate and prevent future polyps which causes gastric side effects in many such patients. Once NSAID treatment is terminated due to such complications, the polyps return, particularly in polyposis syndrome patients.

Compounds such as those disclosed in U.S. Pat. No. 5,643,959 have exhibited advantages in the treatment of neoplastic lesions since such compounds have been shown to induce apotosis in neoplastic cells but not in normal cells in humans. Thus, the severe side effects due to induction of apotosis in normal cells by conventional chemotherapeutics are avoided by these novel therapeutics (see, "Phase I Trial of Sulindac Sulfone in Patients With Familial Polyposis (FAP) With Rectal Polyps: Optimal Dose and Safety," *Digestive Disease Week,* Abstract No. 2457, May 10–16, 1997, American Gastroenterological Association et al.). In addition, such compounds do not exhibit the gastric side effects associated with NSAIDs since such compounds do not substantially inhibit PGE-2. More potent compounds with such neoplasia specificity but without substantial PGE-2 activity are desirable.

SUMMARY OF THE INVENTION

This invention represents potent compounds, that induce apotosis in neoplastic cells (but not substantially in normal cells), for treating patients with neoplastic lesions without substantially inhibiting PGE-2. This invention also involves methods for inducing such specific apotosis in neoplastic cells by exposing such cells to a pharmacologically effective amount of those compounds described below to a patient in need of such treatment. Such compositions are effective in modulating apoptosis and modulating the growth of precancerous lesions and neoplasms, but are not suffering from the side effects of conventional chemotherapeutics and NSAIDs.

DETAILED DESCRIPTION OF THE INVENTION

As discussed above, the present invention includes compounds of Formula I below (as well as their pharmaceutically acceptable salts) for treating a patient with neoplastic, particularly precancerous, lesions:

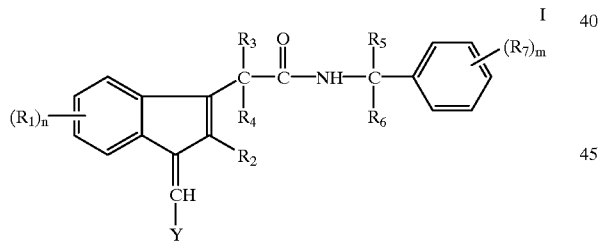

wherein $R_1$ is independently selected in each instance from the group consisting of hydrogen, halogen, lower alkyl, lower alkoxy, amino, lower alkylamino, di-lower alkylamino, lower alkylmercapto, lower alkyl sulfonyl, cyano, carboxamide, carboxylic acid, mercapto, sulfonic acid, xanthate and hydroxy; $R_2$ is selected from the group consisting of hydrogen and lower alkyl;

$R_3$ is selected from the group consisting of hydrogen, halogen, amino, hydroxy, lower alkyl amino, and di-loweralkylamino;

$R_4$ is hydrogen, or $R_3$ and $R_4$ together are oxygen;

$R_5$ and $R_6$ are independently selected from the group consisting of hydrogen, lower alkyl, hydroxy-substituted lower alkyl, amino lower alkyl, lower alkylamino-lower alkyl, lower alkyl amino di-lower alky, lower alkyl nitrile, —$CO_2H$, —$C(O)NH_2$, and a $C_2$ to $C_6$ amino acid;

$R_7$ is independently selected in each instance from the group consisting of hydrogen, amino lower alkyl, lower alkoxy, lower alkyl, hydroxy, amino, lower alkyl amino, di-lower alkyl amino, halogen, —$CO_2H$, —$SO_3H$, —$SO_2NH_2$, and —$SO_2$(lower alkyl);

m and n are integers from 0 to 3 independently selected from one another;

Y is selected from the group consisting of quinolinyl, isoquinolinyl, pyridinyl, pyrimidinyl, pyrazinyl, imidazolyl, indolyl, benzimidazolyl, triazinyl, tetrazolyl, thiophenyl, furanyl, thiazolyl, pyrazolyl, or pyrrolyl, or subsituted variants thereof wherein the substituents are one or two selected from the group consisting of halogen, lower alkyl, lower alkoxy, amino, lower alkylamino, di-lower alkylamino, hydroxy, —$SO_2$(lower alkyl) and —$SO_2NH_2$.

Preferred compounds of this invention for use with the methods described herein include those of Formula I where:

$R_1$ is selected from the group consisting of halogen, lower alkoxy, amino, hydroxy, lower alkylamino and di-loweralkylamino, preferably halogen, lower alkoxy, amino and hydroxy;

$R_2$ is lower alkyl;

$R_3$ is selected from the group consisting of hydrogen, halogen, hydroxy, amino, lower alkylamino and di-loweralkylamino, preferably, hydrogen, hydroxy and lower alkylamino;

$R_5$ and $R_6$ are independently selected from the group consisting of hydrogen, hydroxy-substituted lower alkyl, amino lower alkyl, lower alkylamino-lower alkyl, lower alkyl amino di-lower alkyl, —$CO_2H$, —$C(O)NH_2$; preferably hydrogen, hydroxy-substituted lower alkyl, lower alkyl amino di-lower alkyl, —$CO_2H$, and —$C(O)NH_2$;

$R_7$ is independently selected in each instance from the group consisting of hydrogen, lower alkoxy, hydroxy, amino, lower alkyl amino, di-lower alkyl amino, halogen, —$CO_2H$, —$SO_3H$, —$SO_2NH_2$, and —$SO_2$(lower alkyl); preferably hydrogen, lower alkoxy, hydroxy, amino, amino lower alkyl, halogen, —$CO_2H$, —$SO_3H$, —$SO_2NH_2$, and —$SO_2$(lower alkyl);

Preferably, at least one of the $R_7$ substituents is para- or ortho-located; most preferably ortho-located;

Y is selected from the group consisting of quinolinyl, isoquinolinyl, pyridinyl, pyrimidinyl and pyrazinyl or said substituted variants thereof.

Preferably, the substituents on Y are one or two selected from the group consisting of lower alkoxy, amino, lower alkylamino, di-lower alkylamino, hydroxy, —$SO_2$(lower alkyl) and —$SO_2NH_2$; most preferably lower alkoxy, di-lower alkylamino, hydroxy, —$SO_2$(lower alkyl) and —$SO_2NH_2$.

The present invention also is a method of treating a patient with such lesions by administering to a patient a pharmacologically effective amount of a pharmaceutical composition that includes a compound of Formula I, wherein $R_1$ through $R_7$ and Y are as defined above. Preferably, this composition is administered without therapeutic amounts of an NSAID.

The present invention is also a method of treating individuals with neoplastic lesions by administering a pharmacologically effective amount of an enterically coated pharmaceutical composition that includes compounds of this invention.

Also, the present invention is a method of inhibiting the growth of neoplastic cells by exposing the cells to an effective amount of compounds of Formula I, wherein $R_1$ through $R_7$ and Y are defined as above.

In still another form, the invention is a method of inducing apoptosis in human cells by exposing those cells to an effective amount of compounds of Formula I, wherein $R_1$ through $R_7$ and Y are defined as above where such cells are sensitive to these compounds.

Additionally, in yet another form, the invention is a method of treating a patient having a disease which would benefit from regulation of apoptosis by treating the patient with an effective amount of compounds of Formula I, wherein $R_1$ through $R_8$ are defined as above. The regulation of apoptosis is believed to play an important role in diseases associated with abnormalities of cellular growth patterns such as benign prostatic hyperplasia, neurodegenerative diseases such as Parkinson's disease, autoimmune diseases including multiple sclerosis and rheumatoid arthritis, infectious diseases such as AIDS, and other diseases, as well.

Compounds of this invention are also inhibitors of cGMP-specific phosphodiesterase activity found in neoplastic cells. Such phosphodiesterases include PDE5 as well as the novel PDE disclosed in U.S. patent application Ser. No. 09/173,375 filed Oct. 15, 1998 to Pamukcu et al. For convenience, the PDE inhibitory activity of such compounds can be tested as taught in co-pending U.S. patent application Ser. No. 09046,739 filed Mar. 24, 1998 to Pamukcu et al., which is incorporated herein by reference. Thus, compounds of this invention are useful inhibitors of PDE5 and may be useful in medical indications where inhibition of that enzyme activity is desired.

As used herein, the term "precancerous lesion" includes syndromes represented by abnormal neoplastic, including dysplastic, changes of tissue. Examples include dysplasic growths in colonic, breast, bladder or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), esophagus, prostatic dysplasia, bronchial dysplasia, breast, bladder and/or skin and related conditions (e.g., actinic keratosis), whether the lesions are clinically identifiable or not.

As used herein, the term "carcinomas" refers to lesions that are cancerous. Examples include malignant melanomas, breast cancer, prostate cancer and colon cancer.

As used herein, the term "neoplasm" refers to both precancerous and cancerous lesions and hyperplasia.

As used herein, the term "halo" or "halogen" refers to chloro, bromo, fluoro and iodo groups, and the term "alkyl" refers to straight, branched or cyclic alkyl groups and to substituted aryl alkyl groups. The term "lower alkyl" refers to $C_1$ to $C_8$ alkyl groups.

The term "hydroxy-substituted lower alkyl" refers to lower alkyl groups that are substituted with at least one hydroxy group, preferably no more than three hydroxy groups.

The term "—$SO_2$(lower alkyl)" refers to a sulfonyl group that is substituted with a lower alkyl group.

The term "lower alkoxy" refers to alkoxy groups having from 1 to 8 carbons, including straight, branched or cyclic arrangements.

The term "lower alkylmercapto" refers to a sulfide group that is substituted with a lower alkyl group; and the term "lower alkyl sulfonyl" refers to a sulfone group that is substituted with a lower alkyl group.

The term "pharmaceutically acceptable salt" refers to non-toxic acid addition salts and alkaline earth metal salts of the compounds of Formula I. The salts can be prepared in situ during the final isolation and purification of such compounds, or separately by reacting the free base or acid functions with a suitable organic acid or base, for example. Representative acid addition salts include the hydrochloride, hydrobromide, sulfate, bisulfate, acetate, valerate, oleate, palmatate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali and alkaline earth metal salts include the sodium, calcium, potassium and magnesium salts.

It will be appreciated that certain compounds of Formula I can possess an asymmetric carbon atom and are thus capable of existing as enantiomers. Unless otherwise specified, this invention includes such enantiomers, including any racemates. The separate enaniomers may be synthesized from chiral starting materials, or the racemates can be resolved by conventional procedures that are well known in the art of chemistry such as chiral chromatography, fractional cyrstallization of diastereomeric salts and the like.

Compounds of Formula I also can exist as geometrical isomers (Z and E); the Z isomer is preferred.

Compounds of this invention may be formulated into pharmaceutical compositions together with pharmaceutically acceptable carriers for oral administration in solid or liquid form, or for rectal or topical administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for topical administration include DMSO, alcohol or propylene glycol and the like that can be employed with patches or other liquid-retaining material to hold the medicament in place on the skin so that the medicament will not dry out.

Pharmaceutically acceptable carriers for rectal administration are preferably suppositories that may contain, in addition to the compounds of this invention excipients such as cocoa butter or a suppository wax, or gel.

The pharmaceutically acceptable carrier and compounds of this invention are formulated into unit dosage forms for administration to a patient. The dosage levels of active ingredient (i.e., compounds of this invention) in the unit dosage may be varied so as to obtain an amount of active ingredient effective to achieve lesion-eliminating activity in accordance with the desired method of administration (i.e., oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day.

The pharmaceutical compositions of this invention are preferably packaged in a container (e.g., a box or bottle, or both) with suitable printed material (e.g., a package insert) containing indications, directions for use, etc.

There are several general schemes for producing compounds useful in this invention. One general scheme (which has several sub-variations) involves the case where both $R_3$ and $R_4$ are both hydrogen. This first scheme is described immediately below in Scheme I. The other general scheme (which also has several sub-variations) involves the case where at least one of $R_3$ and $R_4$ is a moiety other than hydrogen but within the scope of Formula I above. This second scheme is described below as "Scheme II."

The general scheme for preparing compounds where both $R_3$ and $R_4$ are both hydrogen is illustrated in Scheme I, which is described in part in U.S. Pat. No. 3,312,730, which is incorporated herein by reference. In Scheme I, $R_1$ is as defined in Formula I above. However, in Scheme I, that substituent can also be a reactive moiety (e.g. a nitro group) that later can be reacted to make a large number of other substituted indenes from the nitro-substituted indenes.

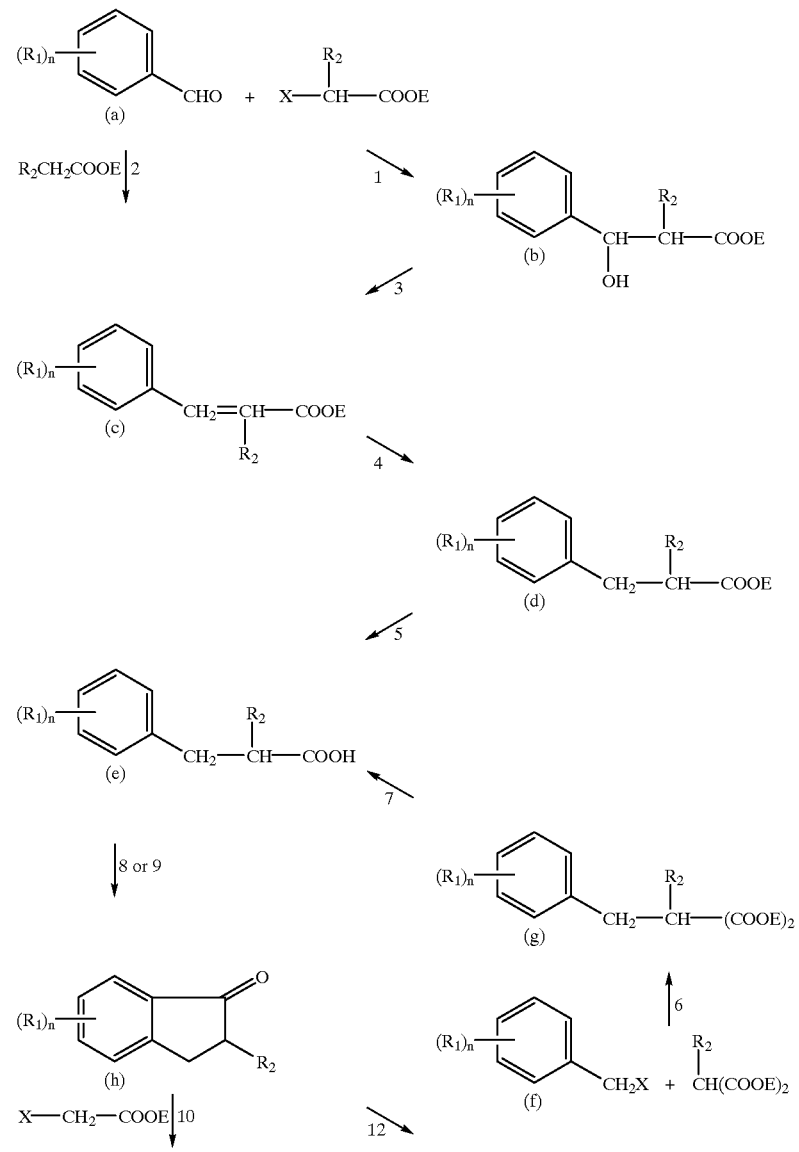

Scheme I

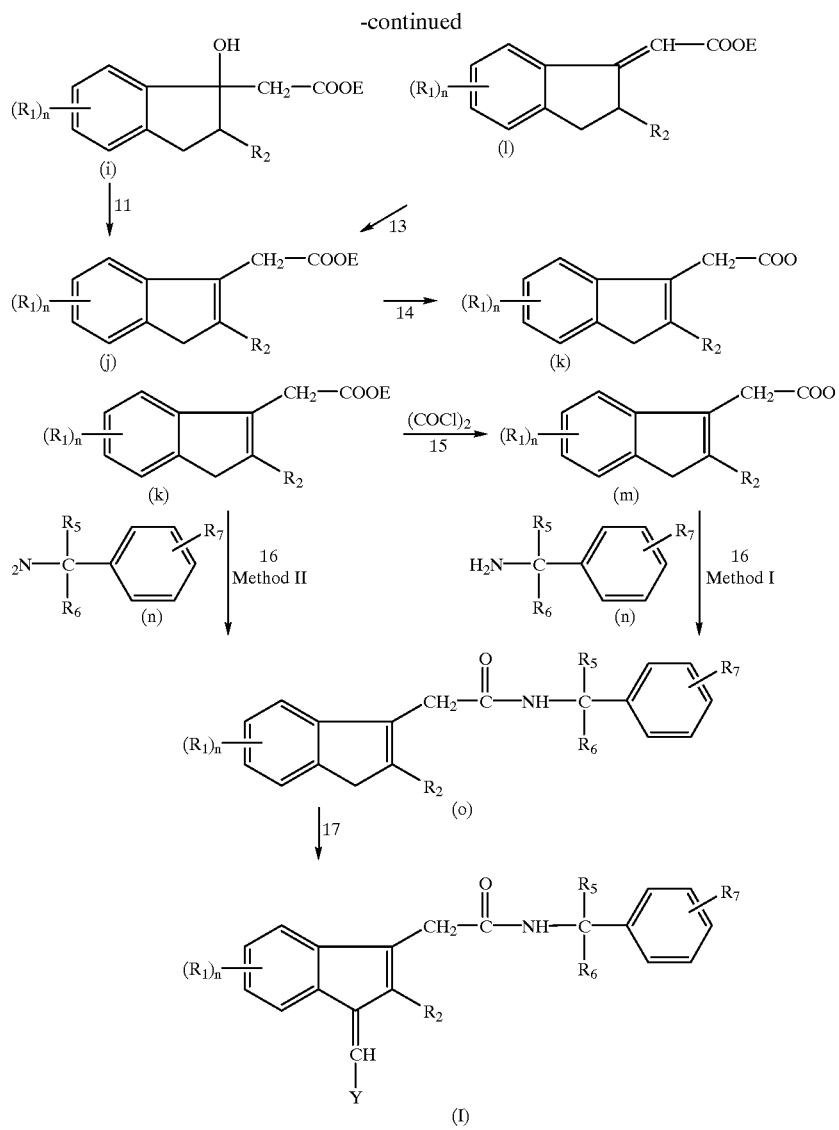

In Scheme I, several sub-variations can be used. In one sub-variation, a substituted benzaldehyde (a) may be condensed with a substituted acetic ester in a Knoevenagel reaction (see reaction 2) or with an α-halogeno propionic ester in a Reformatsky Reaction (see reactions 1 and 3). The resulting unsaturated ester (c) is hydrogenated and hydrolyzed to give a substituted benzyl proponic acid (e) (see reactions 4 and 5). Alternatively, a substituted malonic ester in a typical malonic ester synthesis (see reactions 6 and 7) and hydrolysis decarboxylation of the resulting substituted ester (g) yields the benzyl propionic acid (e) directly. This latter method is especially preferable for nitro and alkylthio substituents on the benzene ring.

The next step is the ring closure of the β-aryl proponic acid (e) to form an indanone (h) which may be carried out by a Friedel-Crafts Reaction using a Lewis acid catalyst (Cf. Organic Reactions, Vol. 2, p. 130) or by heating with polyphosphoric acid (see reactions 8 and 9, respectively). The indanone (h) may be condensed with an α-halo ester in the Reformatsky Reaction to introduce the aliphatic acid side chain by replacing the carboxyl group (see reaction 10). Alternately, this introduction can be carried out by the use of a Wittig Reaction in which the reagent is a α-triphenylphosphinyl ester, a reagent which replaces the carbonyl with a double bond to the carbon (see reaction 12). This product (1) is then immediately rearranged into the indene (j)(see reaction 13). If the Reformatsky Reaction route is used, the intermediate 3-hydroxy-3-aliphatic acid derivative i must be dehydrated to the indene (j)(see reaction 11).

The indenylacetic acid (k) in THF then is allowed to react with oxalyl or thionyl chloride or similar reagent to produce the acid chloride (m) (see reaction 15), whereupon the solvent is evaporated. There are two methods to carry out reaction 16, which is the addition of the benzylamine side chain (n).

Method (I)

In the first method, the benzylamine (n) is added slowly at room temperature to a solution of 5-fluoro-2-methyl-3-indenylacetyl chloride in $CH_2Cl_2$. The reaction mixture is refluxed overnight, and extracted with aqueous HCl (10%), water, and aqueous $NaHCO_3$ (5%). The organic phase is dried ($Na_2SO_4$) and is evaporated to give the amide compound (o)

Method (II)

In the second method, the indenylacetic acid (k) in DMA is allowed to react with a carbodiimide (e.g. N-(3- dimethylaminopropyl)-N'-ethylcarbodiimide hydrochloride) and benzylamine at room temperature for two days. The reaction mixture is added dropwise to stirred ice water. A yellow precipitate is filtered off, is washed with water, and is dried in vacuo. Recrystallization gives the amide compound (o).

Compounds of the type a' (Scheme III), o (Scheme I), t (Scheme II), y (Scheme IIB) may all be used in the condensation reaction shown in Scheme III.

Substituents

X=halogen, usually Cl or Br.

E=methyl, ethyl or benzyl, or lower acyl.

$R_1$, $R_2$, $R_6$, $R_5$, and $R_7$=as defined in Formula I.

Y, n and m=as defined in Formula I.

Reagents and general conditions for Scheme I (numbers refer to the numbered reactions):

(1) Zn dust in anhydrous inert solvent such as benzene and ether.

(2) $KHSO_4$ or p-toluene sulfonic acid.

(3) $NaOC_2H_5$ in anhydrous ethanol at room temperature.

(4) $H_2$ palladium on charcoal, 40 p.s.i. room temperature.

(5) NaOH in aqueous alcohol at 20–100°.

(6) $NaOC_2H_5$ or any other strong base such as NaH or K-t-butoxide.

(7) Acid.

(8) Friedel-Crafts Reaction using a Lewis Acid catalyst Cf. Organic Reactions, Vol. II, p. 130.

(9) Heat with polyphosphoric acid.

(10) Reformatsky Reaction: Zn in inert solvent, heat.

(11) p-Toluene sulfonic acid and $CaCl_2$ or $I_2$ at 200°

(12) Wittig Reaction using $(C_6H_5)_3$ P=C—COOE 20–80° in ether or benzene

(13) (a) $NBS/CCl_4$/benzoyl peroxide (b) $PtO_2/H_2$(1 atm.)/ acetic acid

(14) (a) NaOH (b) HCl

(15) Oxalyl or thionyl chloride in $CH_2Cl_2$ or THF

(16) Method I: 2 equivalents of $NH_2$—$C(R_5R_6)$—Ph—$(R_7)_m$ Method II: carbodiimide in THF

(17) 1N $NaOCH_3$ in MeOH under reflux conditions

Indanones within the scope of compound (h) in Scheme I are known in the literature and are thus readily available as intermediates for the remainder of the synthesis so that reactions 1–7 can be conveniently avoided. Among such known indanones are:

5-methoxyindanone 6-methoxyindanone 5-methylindanone 5-methyl-6-methoxyindanone 5-methyl-7-chloroindanone 4-methoxy-7-chloroindanone 4-isopropyl-2,7-dimethylindanone 5,6,7-trichloroindanone 2-n-butylindanone 5-methylthioindanone Scheme II has two mutually exclusive sub-schemes: Scheme IIA and Scheme II B. Scheme II A is used when $R_3$ is hydroxy and $R_4$ is hydrogen or when the two substituents form an oxo group. When $R_3$ is lower alkyl amino, Scheme II B is employed.

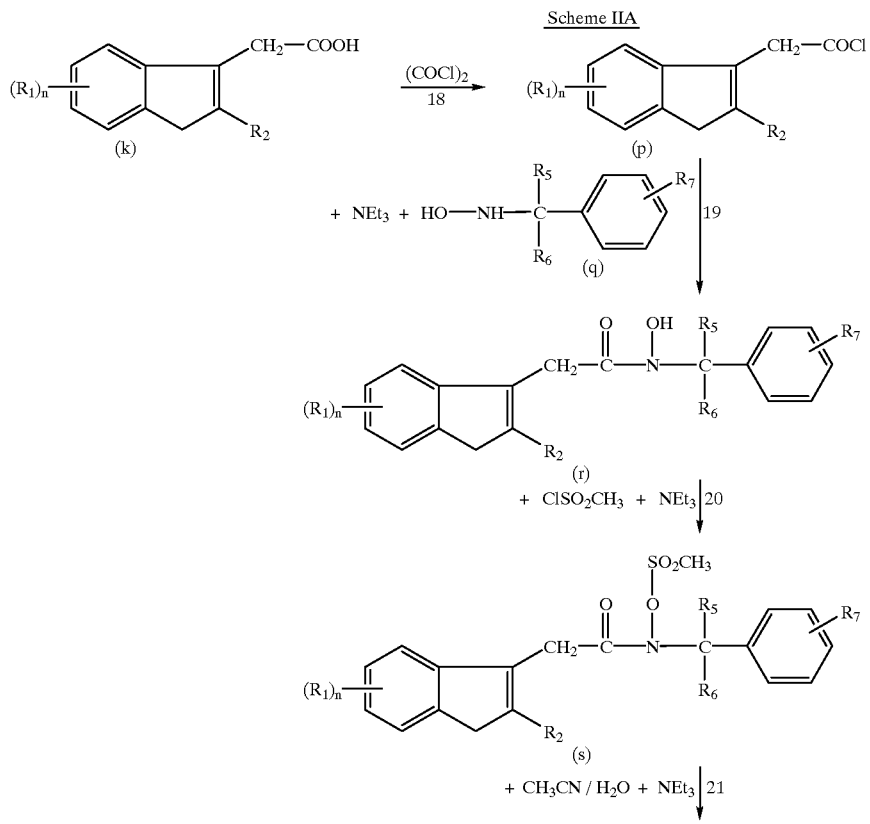

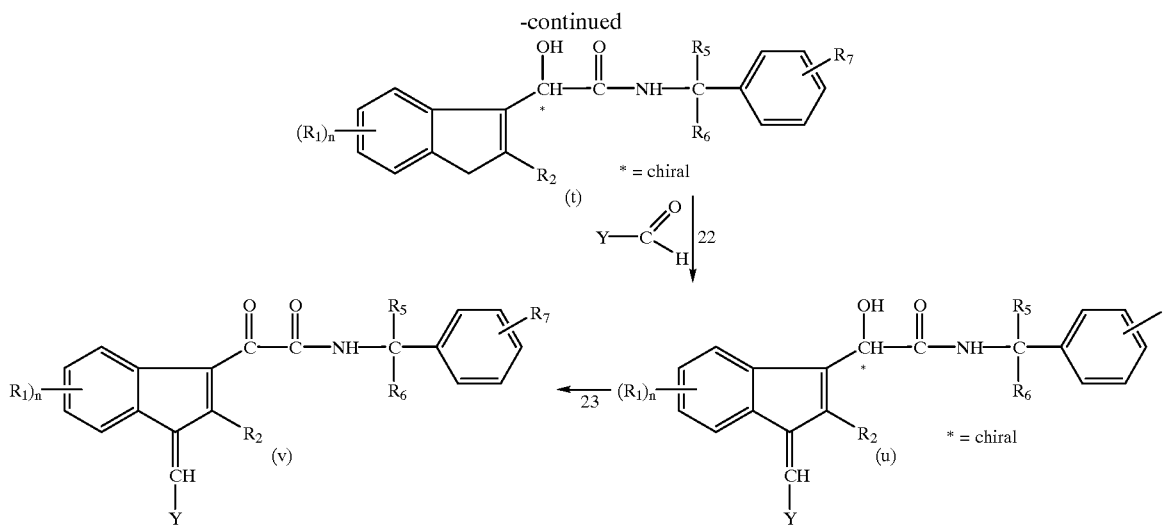

Similar to Scheme I, in Scheme IIA the indenylacetic acid (k) in THF is allowed to react with oxalylchloride under reflux conditions to produce the acid chloride (p) (see reaction 18), whereupon the solvent is evaporated. In reaction 19, a 0° C. mixture of a benzyl hydroxylamine hydrochloride (q) and $Et_3N$ is treated with a cold solution of the acid chloride in $CH_2Cl_2$ over a period of 45–60 minutes. The mixture is warmed to room temperature and stirred for one hour, and is treated with water. The resulting organic layer is washed with 1 N HCl and brine, is dried over magnesium sulfate and is evaporated. The crude product, a N-hydroxy-N-benzyl acetamide (r) is purified by crystallization or flash chromatography. This general procedure is taught by Hoffman et al., JOC 1992, 57, 5700–5707.

The next step is the preparation of the N-mesyloxy amide (s) in reaction 20, which is also taught by Hoffman et al., JOC 1992, 57, 5700–5707. Specifically, to a solution of the hydroxamic acid (r) in $CH_2Cl_2$ at 0° C. is added triethylamine. The mixture is stirred for 10–12 minutes, and methanesulfonyl chloride is added dropwise. The mixture is stirred at 0° C. for two hours, is allowed to warm to room temperature, and is stirred for another two hours. The organic layer is washed with water, 1 N HCl, and brine, and is dried over magnesium sulfate. After rotary evaporation, the product(s) is usually purified by crystallization or flash chromatography.

The preparation of the N-benzyl-α-(hydroxy) amide (t) in reaction 21, is also taught by Hoffman et al., JOC 1992, 57, 5700–5707 and Hoffman et al., JOC 1995, 60, 4121–4125. Specifically, to a solution of the N-(mesyloxy) amide (s) in $CH_3CN/H_2O$ is added triethylamine in $CH_3CN$ over a period of 6–12 hours. The mixture is stirred overnight. The solvent is removed, and the residue is dissolved in ethyl acetate. The solution is washed with water, 1 N HCl, and brine, and is dried over magnesium sulfate. After rotary evaporation, the product (t) is usually purified by recrystallization.

Reaction 22 in Scheme IIA involves a condensation with certain aldehydes, which is described in Scheme III below, a scheme that is common to products made in accordance with Schemes I, IIA and IIB.

The final reaction 23 in Scheme IIA is the preparation of the N-benzyl-α-ketoamide (v), which involves the oxidation of a secondary alcohol (u) to a ketone by e.g. a Pfitzner-Moffatt oxidation, which selectively oxidizes the alcohol without oxidizing the Y group. Compounds (u) and (v) may be derivatized in order to obtain

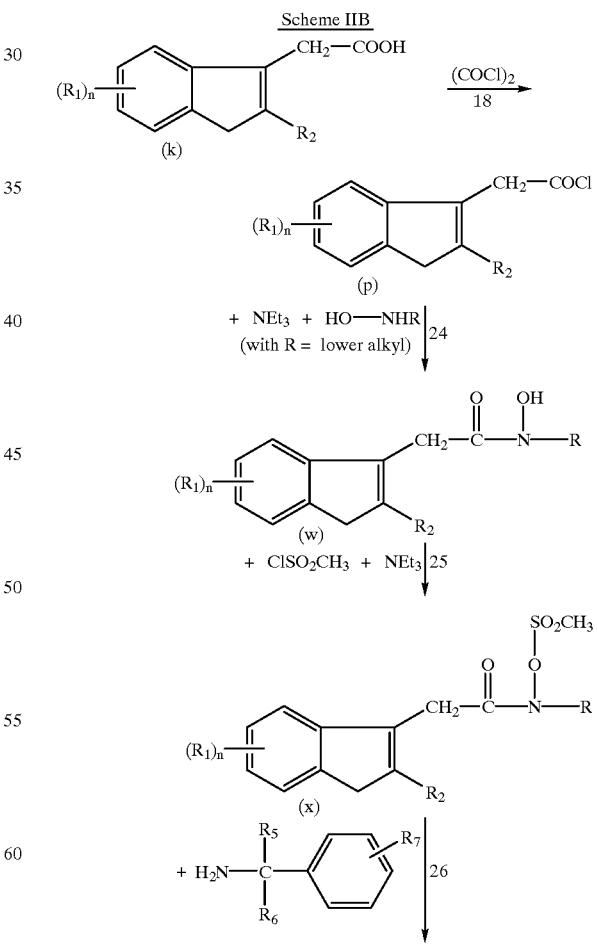

15

-continued

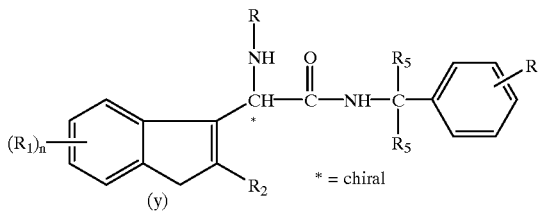

(y)   * = chiral compounds with $R_3$ and $R_4$ groups as set forth in Formula I.

As explained above, Scheme IIB is employed when $R_3$ is lower alkyl amino. Similar to Scheme I, in Scheme IIIB the indenylacetic acid (k) in THF is allowed to react with oxalylchloride under reflux conditions to produce the acid chloride (p) (see reaction 18), whereupon the solvent is evaporated. In reaction 24, a mixture of an alkyl hydroxylamine hydrochloride (i.e. HO—NHR where R is a lower alkyl, preferably isopropyl) and $Et_3N$ is treated at 0° C. with a cold solution of the acid chloride in $CH_2Cl_2$ over a period of 45–60 minutes. The mixture is warmed to room temperature and is stirred for one hour, and is diluted with water. The resulting organic layer is washed with 1 N HCl and brine, is dried over magnesium sulfate and is evaporated. The crude product, a N-hydroxy-N-alkyl acetamide (w) is purified by crystallization or flash chromatography. This general procedure is also taught by Hoffman et al., JOC 1992, 57, 5700–5707

The preparation of the N-mesyloxy amide (x) in reaction 25, which is also taught by Hoffman et al., JOC 1992, 57, 5700–5707. Specifically, a solution of the hydroxamic acid (w) in $CH_2Cl_2$ at 0° C. is treated with triethylamine, is stirred for 10–12 minutes, and is treated dropwise with methanesulfonyl chloride. The mixture is stirred at 0° C. for two hours, is allowed to warm to room temperature, and is stirred for another two hours. The resulting organic layer is washed with water, 1 N HCl, and brine, and is dried over magnesium sulfate. After rotary evaporation, the product (x) is usually purified by crystallization or flash chromatography.

The preparation of the N-benzyl indenyl-α-loweralkylamino- acetamide compound (y) in Scheme IIB as taught by Hoffman et al., JOC 1995, 60, 4121–25 and J. Am. Chem Soc. 1993, 11, 5031–34, involves the reaction of the N-mesyloxy amide (x), with a benzylamine in $CH_2Cl_2$ at 0° C. is added over a period of 30 minutes. The resulting solution is stirred at 0° C. for one hour and at room temperature overnight. The solvent is removed, and the residue is treated with 1 N NaOH. The extract with $CH_2Cl_2$ is washed with water and is dried over magnesium sulfate. After rotary evaporation, the product (y) is purified by flash chromatography or crystallization.

Scheme III

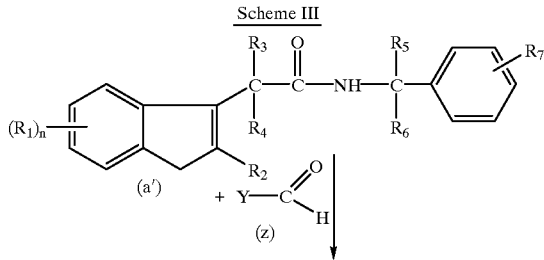

16

-continued

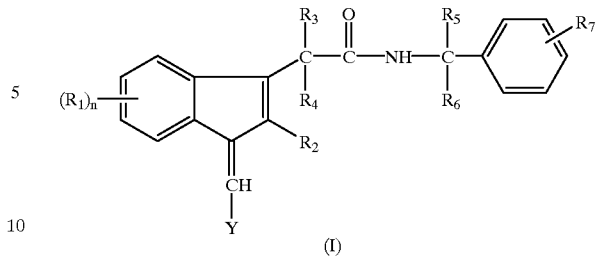

(I)

Scheme III involves the condensation of the heterocycloaldehydes (i.e. Y—CHO) with the indenyl amides to produce the final compounds of Formula I. This condensation is employed, for example, in reaction 17 in Scheme I above and in reaction 22 in Scheme IIIA. It is also used to convert compound (y) in Scheme IIB to final compounds of Formula I.

In Scheme III, the amide (a') from the above schemes, a N-heterocycloaldehyde (z), and sodium methoxide (1 M in methanol) are stirred at 60° C. under nitrogen for 24 hours. After cooling, the reaction mixture is poured into ice water. A solid is filtered off, is washed with water, and is dried in vacuo. Recrystallization provides a compound of Formula I in Schemes I and IIB and the intermediate (u) in Scheme IIA.

As has been pointed out above, it is preferable in the preparation of many types of the compounds of this invention, to use a nitro substituent on the benzene ring of the indanone nucleus and convert it later to a desired substituent since by this route a great many substituents can be reached. This is done by reduction of the nitro to the amino group followed by use of the Sandmeyer Reaction to introduce chlorine, bromine, cyano or xanthate in place of the amino. From the cyano derivatives hydrolysis yields the carboxamide and carboxylic acid; other derivatives of the carboxy group such the esters can then be prepared. The xanthates, by hydrolysis, yield the mercapto group that may be oxidized readily to the sulfonic acid or alkylated to an alkylthio group which can then be oxidized to alkylsulfonyl groups. These reactions may be carried out either before or after the introduction of the 1-substituent.

The foregoing may be better understood from the following examples that are presented for purposes of illustration and are not intended to limit the scope of the invention. As used in the following examples, the references to substituents such as $R_1$, $R_2$, etc., refer to the corresponding compounds and substituents in Formula I above.

EXAMPLE 1

(Z)-5-Fluoro-2-Methyl-(-4-Pyridinylidene)-3-(N-Benzyl)-Indenylacetamide (A) p-Fluoro-α-methylcinnamic acid p-Fluorobenzaldehyde (200 g, 1.61 mol), propionic anhydride (3.5 g, 2.42 mol) and sodium propionate (155 g, 1.61 mol) are mixed in a one liter three-necked flask which had been flushed with nitrogen. The flask is heated gradually in an oil-bath to 140° C. After 20 hours, the flask is cooled to 100° C. and poured into 8 l of water. The precipitate is dissolved by adding potassium hydroxide (302 g) in 2l of water. The aqueous solution is extracted with ether, and the ether extracts are washed with potassium hydroxide solution. The combined aqueous layers are filtered, are acidified with concentrated HCl, and are filtered. The collected solid, p-fluoro-α-methylcinnamic acid, is washed with water, and is dried and used as obtained.

(B) p-Fluoro-α-methylhydrocinnamic acid

To p-fluoro-α-methylcinnamic acid (177.9 g, 0.987 mol) in 3.6 l ethanol is added 11.0 g of 5% Pd/C. The mixture is reduced at room temperature under a hydrogen pressure of 40 p.s.i. When hydrogen uptake ceases, the catalyst is filtered off, and the solvent is evaporated in vacuo to give the product, p-fluoro-α-methylhydrocinnamic acid, which was used directly in the next step.

(C) 6-Fluoro-2-methylindanone

To 932 g polyphosphoric acid at 70° C. (steam bath) is added p-fluoro-α-methylhydrocinnamic acid (93.2 g, 0.5 mol) slowly with stirring. The temperature is gradually raised to 95° C., and the mixture is kept at this temperature for 1 hour. The mixture is allowed to cool and is added to 2 l. of water. The aqueous suspension is extracted with ether. The extract is washed twice with saturated sodium chloride solution, 5% $Na_2CO_3$ solution, and water, and is dried, and is concentrated on 200 g silica-gel; the slurry is added to a five pound silica-gel column packed with 5% ether-petroleum ether. The column is eluted with 5–10% ether-petroleum ether, to give 6-fluoro-2-methylindanone. Elution is followed by TLC.

(D) 5-fluoro-2-methylindenyl-3-acetic acid

A mixture of 6-fluoro-2-methylindanone (18.4 g, 0.112 mol), cyanoacetic acid (10.5 g, 0.123 mol), acetic acid (6.6 g), and ammonium acetate (1.7 g) in dry toluene (15.5 ml) is refluxed with stirring for 21 hours, as the liberated water is collected in a Dean Stark trap. The toluene is evaporated, and the residue is dissolved in 60 ml of hot ethanol and 14 ml of 2.2 N aqueous potassium hydroxide solution. 22 g of 85% KOH in 150 ml of water is added, and the mixture refluxed for 13 hours under nitrogen. The ethanol is removed under vacuum, and 500 ml water is added. The aqueous solution is extracted well with ether, and is then boiled with charcoal. The aqueous filtrate is acidified to pH 2 with 50% cold hydrochloric acid. The precipitate is dried and 5-fluoro-2-methylindenyl-3-acetic acid (M. P. 164–166° C.) is obtained.

(E) 5-fluoro-2-methylindenyl-3-acetyl chloride 5-fluoro-2-methylindenyl-3-acetic acid (70 mmol) in THF (70 ml) is allowed to react with oxalylchloride (2 M in $CH_2Cl_2$; 35 ml; 70 mmol) under reflux conditions (24 hours). The solvent is evaporated to yield the title compound, which is used as such in the next step.

(F) 5-Fluoro-2-methyl-3-benzyl)-indenylacetamide

Benzylamine (5 mmol) is added slowly at room temperature to a solution of 5-fluoro-2-methylindenyl-3-acetyl chloride (2.5 mmol.) in $CH_2Cl_2$ (10 ml). The reaction mixture is refluxed overnight, and is extracted with aqueous HCl (10%), water, and aqueous $NaHCO_3$ (5%). The organic phase is dried ($Na_2SO_4$) and is evaporated to give the title compound, which is recrystallized from $CH_2Cl_2$ to give the title compound as a white solid (m.p. 144° C.).

(G) (Z)-5-Fluoro-2-methyl-(4-pyridinylidene)-3-(N-benzyl)-indenylacetamide 5-fluoro-2-methyl-3-(N-benzyl)-indenylacetamide (3.38 mmol), 4-pyridinecarboxaldehyde (4 mmol), sodium methoxide (1M $NaOCH_3$ in methanol (30 ml)) are heated at 60° C. under nitrogen with stirring for 24 hours. After cooling, the reaction mixture is poured into ice water (200 ml). A solid is filtered off, washed with water, and dried in vacuo. Recrystallization from $CH_3CN$ gives the title compound (m.p. 202° C.) as a yellow solid ($R_1$=F, $R_2$=$CH_3$, $R_3$=H, $R_4$=H, $R_5$=H, $R_7$=H, n=1, m=1, Y=4-pyridinyl).

(H) (E)-5-Fluoro-2-methyl-(4-pyridinylidene)-3-(N-benzyl)-indenylacetamide

The mother liquor obtained from the $CH_3CN$ recrystallization of 1G is rich on the geometrical isomer of 1G. The E-isomer can be obtained pure by repeated recrystallizations from $CH_3CN$.

EXAMPLE 2

(Z)-5-Fluoro-2-Methyl-(3-Pyridinylidene)-3-(N-Benzyl)-Indenylacetamide

This compound is obtained from 5-fluoro-2-methyl-3-(N-benzyl)-indenylacetamide (Example 1F) using the procedure of Example 1, part G and replacing 4-pyridinecarboxaldehyde with 3-pyridinecarboxaldehyde. Recrystallization from $CH_3CN$ gives the title compound (m.p. 175° C.)($R_1$=F, $R_2$=$CH_3$, $R_3$=H, $R_4$=H, $R_5$=H, $R_6$=H, $R_7$=H, n=1, m=1, Y=3-pyridinyl).

EXAMPLE 3

(Z)-5-Fluoro-2-Methyl-(2-Pyridinylidene)-3-(N-Benzyl)-Indenylacetamide

This compound is obtained from 5-fluoro-2-methyl-3-(N-benzyl)-indenylacetamide (Example 1F) using the procedure of Example 1, part G and replacing 4-pyridinecarboxaldehyde with 2-pyridinecarboxaldehyde. Recrystallization from ethylacetate gives the title compound (m.p. 218° C.)($R_1$=F, $R_2$=$CH_3$, $R_3$=H, $R_4$=H, $R_5$=H, $R_6$=H, $R_7$=H, n=1, m=1, Y=2-pyridinyl).

EXAMPLE 4

(Z)-5-Fluoro-2-Methyl-(4-Quinolinylidene)-3-(N-Benzyl)-Indenylacetamide

This compound is obtained from 5-fluoro-2-methyl-3-(N-benzyl)-indenylacetamide (Example 1F) using the procedure of Example 1, part G and replacing 4-pyridinecarboxaldehyde with 4-quinolinecarboxaldehyde. Recrystallization from ethylacetate gives the title compound (m.p. 239° C.)($R_1$=F, $R_2$=$CH_3$, $R_3$=H, $R_4$=H, $R_5$=H, $R_6$=H, $R_7$=H, n=1, m=1, Y=4-quinolinyl).

EXAMPLE 5

(Z)-5-Fluoro-2-Methyl-(4,6-Dimethyl-2-Pyridinylidene)-3-(N-Benzyl)-Indenylacetamide 5-Fluoro-2-methyl-3-(N-benzyl)-indenylacetamide from Example 1, part F is allowed to react with 4,6-dimethyl-2-pyridinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=4,6-dimethyl-2-pyridinyl).

EXAMPLE 6

(Z)-5-Fluoro-2-Methyl-(3-Quinolinylidene,-3-(N-Benzyl)-Indenylacetamide

5-Fluoro-2-methyl-3-(N-benzyl)-indenylacetamide from Example 1, part F is allowed to react with 3-quinolinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y =3-quinolinyl),

EXAMPLE 7

(Z)-5 -Fluoro-2-Metbyl-(2-Quinolinylidene)-3-(N-Benzyl)-Indenylacetamide

5-Fluoro-2-methyl-3-(N-benzyl)-indenylacetamide from Example 1, part F is allowed to react with 2-quinolinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=2-quinolinyl).

EXAMPLE 8

(Z)-5-Fluoro-2-Methyl-(Pyrazinylidene)-3-(N-Benzyl)-Indenylacetamide

5-Fluoro-2-methyl-3-(N-benzyl)-indenylacetamide from Example 1, part F is allowed to react with pyrazinealdehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=pyrazinyl).

EXAMPLE 9

(Z)-5-Fluoro-2-Methyl-(3-Pyridazinylidene)-3-(N-Benzyl)-Indenylacetamide

5-Fluoro-2-methyl-3-(N-benzyl)-indenylacetamide from Example 1, part F is allowed to react with pyridazine-3-aldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=3-pyridazinyl).

EXAMPLE 10

(Z)-5-Fluoro-2-Methyl-(4-Pyrimidinylidene)-3-(N-Benzyl)-Indenylacetamide

5-Fluoro-2-methyl-3-(N-benzyl)-indenylacetamide from Example 1, part F is allowed to react with pyrimidine-4-aldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=4-pyrimidinyl).

EXAMPLE 11

(Z)-5-Fluoro-2-Methyl-(2-Methyl-4-Pyrimidinylidene)-3-(N-Benzyl)-Indenylacetamide 5-Fluoro-2-methyl-3-(N-benzyl)-indenylacetamide from Example 1, part F is allowed to react with 2-methyl-pyrimidine-4-aldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=2-methyl-4-pyrimidinyl).

EXAMPLE 12

(Z)-5-Fluoro-2-Methyl-(-4-Pyridazinylidene)-3-(N-Benzyl)-Indenylacetamide

5-Fluoro-2-methyl-3-(N-benzyl)-indenylacetamide from Example 1, part F is allowed to react with pyridazine-4-aldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=4-pyridazinyl).

EXAMPLE 13

(Z)-5-Fluoro-2-Methyl-(1-Methyl-3-Indolylidene)-3-(N-Benzyl)-Indenylacetamide

5-Fluoro-2-methyl-3-(N-benzyl)-indenylacetamide from Example 1, part F is allowed to react with 1-methylindole-3-carboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=1-methyl-3-indolyl).

EXAMPLE 14

(Z)-5-Fluoro-2-Methyl-(1-Acetyl-3-Indolylidene)-3-(N-Benzyl)-Indenylacetamide

5-Fluoro-2-methyl-3-(N-benzyl)-indenylacetamide from Example 1, part F is allowed to react with 1-acetyl-3-indolecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=1-acetyl-3-indolyl).

EXAMPLE 15

(Z)-5-Fluoro-2-Methyl-(4-Pyridinylidene)-3-(N-2-Fluorobenzyl)-Indenylacetamide (A) 5-Fluoro-2-methyl-3-(N-2-fluorobenzyl)-indenylacetamide This compound is obtained from 5-fluoro-2-methylindenyl-3-acetyl chloride (Example 1E) using the procedure of Example 1, Part F and replacing benzylamine with 2-fluorobenzylamine.

(B) (Z)-5-Fluoro-2-methyl-(4-pyridinylidene)-3-(N-2-fluorobenzyl)-indenylacetamide 5-Fluoro-2-methyl-3-(N-2-fluorobenzyl)-indenylacetamide is allowed to react with 4-pryidinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=4-pyridinyl).

EXAMPLE 16

(Z)-5-Fluoro-2-Methyl-(3-Pyridinylidene)-3-(N-2-Fluorobenzyl)-Indenylacetamide

5-Fluoro-2-methyl-3-(N-2-fluorobenzyl)-indenylacetamide from Example 15, -part A is allowed to react with 3-pryidinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=3-pyridinyl).

EXAMPLE 17

(Z)-5-Fluoro-2-Methyl-(2-Pyridinylidene)-3-(N-2-Fluorobenzyl)-Indenylacetamide

5-Fluoro-2-methyl-3-(N-2-fluorobenzyl)-indenylacetamide from Example 15, part A is allowed to react with 2-pyridinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=2-pyridinyl).

EXAMPLE 18

(Z)-5-Fluoro-2-Methyl-(4-Quinolinylidene)-3-(N-2-Fluorobenzyl)-Indenylacetamide

5-Fluoro-2-methyl-3-(N-2-fluorobenzyl)-indenylacetamide from Example 15, part A is allowed to react with 4-quinolinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=3-quinolinyl).

EXAMPLE 19

(Z)-5-Fluoro-2-Methyl-(3-Pyrazinylidene)-3-(N-2-Fluorobenzyl)-Indenylacetamide

5-Fluoro-2-methyl-3-(N-2-fluorobenzyl)-indenylacetamide from Example 15, part A is allowed to react with pyrazinealdehyde according to the procedure of Example 1, Part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=3-pyrazinyl).

EXAMPLE 20

(Z)-5-Fluoro-2-Methyl-(3-Pyridazinylidene)-3-(N-2-Fluorobenzyl)-Indenylacetamide 5-Fluoro-2-methyl-3-(N-2-fluorobenzyl)-indenylacetamide from Example 15, part A is allowed to react with 3-pryidaziine-3-aldehyde according to the procedure of Example 1, Part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=3-pyridazinyl).

EXAMPLE 21

(Z)-5-Fluoro-2-Methyl-(3-Pyrimidinylidene)-3-(N-2-Fluorobenzyl)-Indenylacetamide 5-Fluoro-2-methyl-3-(N-2-fluorobenzyl)-indenylacetamide from Example 15, part A is allowed to react with pryimidine-4-aldehyde according to the procedure of Example 1, Part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=3-pyrimidinyl).

EXAMPLE 22

(Z)-5-Fluoro-2-Methyl-(4-Pyridazinylidene)-3-(N-2-Fluorobenzyl)-Indenylacetamide 5-Fluoro-2-methyl-3-(N-2-fluorobenzyl)-indenylacetamide from Example 15, part A is allowed to react with pryidazine-4-aldehyde according to the procedure of Example 1, Part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=4-pyridazinyl).

EXAMPLE 23

(Z)-5-Fluoro-2-Methyl-(4-Pyridinylidene)-3-(N-(S-α-Hydroxymethyl)Benzyl)-Indenylacetamide (A) 5-Fluoro-2-methyl-3-(N-(S-α-hydroxylmethylybenzyl)-indenylacetamide 5-Fluoro-2-methylindenyl-3-acetic acid (from Example 1 D) (2.6 mmol) in DMA (2 ml) is allowed to react with n-(3-dimethylaminopropyl)-N'-ethylcarbodiimide chloride (4 mmol) and S-2-amino-2-phenylethanol (3.5 mmol) at room temperature for two days. The reaction mixture is added dropwise to stirred ice water (50 ml). A white precipitate is filtered off, washed with water (5 ml), and dried in vacuo. Recrystallization from ethylacetate gives the desired compound.

(B) (Z)-5-fluoro-2-methyl-(4-pyridinylidene)-3-(N(S-α-hydroxymethyl)benzyl)-indenylacetamide 5-Fluoro-2-methyl-3-(N-(S-α-hydroxylmethyl)benzyl)-indenylacetamide from part A is allowed to react with 4-pryidinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=4-pyridinyl).

EXAMPLE 24

(Z)-5-Fluoro-2-Methyl-(3-Pyridinylidene)-3-(N-(S-α-Hydroxymethyl)Benzyl)-Indenylacetamide 5-Fluoro-2-methyl-3-(N-(S-α-hydroxylmethyl)benzyl)-indenylacetamide from Example 23 part A is allowed to react with 3-pryidinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=3-pyridinyl).

EXAMPLE 25

(Z)-5-Fluoro-2-Methyl-(2-Pyridinylidene)-3-(N-(S-α-Hydroxymethyl)Benzyl)-Indenylacetamide 5-Fluoro-2-methyl-3-(N-(S-α-hydroxylmethyl)benzyl)-indenylacetamide from Example 23 part A is allowed to react with 2-pryidinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=2-pyridinyl).

EXAMPLE 26

(Z)-5-Fluoro-2-Methyl-(4-Quinolinylidene)-3-(N-(S-α-Hydroxymethyl)Benzyl-Indenylacetamide 5-Fluoro-2-methyl-3-(N-(S-α-hydroxylmethyl)benzyl)-indenylacetamide from Example 23 part A is allowed to react with 4quinolinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=4-quinolinyl).

EXAMPLE 27

(Z)-5-Fluoro-2-Methyl-(Pyrazidinylidene)-3-(N-(S-α-Hydroxymethyl)Benzyl)-Indenylacetamide 5-Fluoro-2-methyl-3-(N-(S-α-hydroxylmethyl)benzyl)-indenylacetamide from Example 23 part A is allowed to react with pryazidinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=pyrazidinyl).

EXAMPLE 28

(Z)-5-Fluoro-2-Methyl-(3-Pyridazinylidene)-3-(N-(S-α-Hydroxymethyl)Benzyl)-Indenylacetamide 5-Fluoro-2-methyl-3-(N-(S-α-hydroxylmethyl)benzyl)-indenylacetamide from Example 23 part A is allowed to react with pryidazine-3-aldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=3-pyridazinyl).

EXAMPLE 29

(Z)-5-Fluoro-2-Methyl-(4-Pyrimidinylidene)-3-(N-(S-α-Hydroxymethyl)Benzyl)-Indenylacetamide 5-Fluoro-2-methyl-3-(N-(S-α-hydroxylmethyl)benzyl)-indenylacetamide from Example 23 part A is allowed to react with pryimidine-4-aldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=4-pyrimidinyl).

EXAMPLE 30

(Z)-5-Fluoro-2-Methyl-(4-Pyridazinylidene)-3-(N-(S-α-Hydroxymethyl)Benzyl)-Indenylacetamide 5-Fluoro-2-methyl-3-(N-(S-α-hydroxylmethyl)benzyl)-Indenylacetamide from Example 23 part A is allowed to react with pryidazine-4-aldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=4-pyridazinyl).

EXAMPLE 31 rac-(Z)-5-Fluoro-2-Methyl-(4-Pyridinylidene)-3 -(N-Benzyl)Indenyl-α-Hydroxyacetamide (A) 5-fluoro-2-methyl-3-(N-benzyl-N-hydroxy)-indenylacetamide To a mixture of N-benzylhydroxylamine hydrochoride (12 mmol) and $Et_3N$ (22 mmol) in $CH_2Cl_2$ (100 ml) at 0° C. is added a cold solution of 5-fluoro-2-methylindenyl-3-acetyl chloride (Example 1, Step E) (10 mmol) in $CH_2Cl_2$ (75 ml) over a period of 45–60 minutes. The mixture is warmed to room temperature and is stirred for 1 hour. The mixture is diluted with water (100 ml), and the organic layer is washed with HCl (2×25 ml) and brine (2×100 ml), dried ($MgSO_4$) and evaporated. The crude product is purified with flash chromatography to give the title compound.
(B) 5-Fluoro-2-methyl-3-(N-benzyl-N-mesyloxy)-indenylacetamide To a solution of 5-fluoro-2-methyl-3-(N-benzyl-N-hydroxy)-indenylacetamide (5 mmol) in $CH_2Cl_2$ (25 ml) at 0° C. is added triethylamine (5 mmol). The mixture is stirred for 10 minutes, and methanesulfonyl chloride (5.5 mmol) is added dropwise. The solution is stirred at 0° C. for 2 hours, allowed to warm to room temperature, and stirred for another 2 hours. The organic layer is washed with water (2×20 ml), in HCl (15 ml), and brine (20 ml) and dried over $MgSO_4$. After rotary evaporation, the product is purified with flash chromatography to give the title compound.
(C) rac-5-Fluoro-2-methyl-3-(N-benzyl)-α-hydroxyindenylacetamide To a solution of 5-fluoro-2-methyl-3-(N-benzyl-N-mesyloxy)-indenylacetamide (2 mmol) in $CH_3CN/H_2O$ (12 ml. each) is added triethylamine (2.1 mmol) in $CH_3CN$ (24 ml) over a period of 6 hours. The mixture is stirred overnight The solvent is removed, and the residue diluted with ethyl acetate (60 ml), washed with water (4×20 ml), in HCl (15 ml), and brine (20 ml) and dried over $MgSO_4$. After rotary evaporation, the product is purified by recrystallization to give the title compound.
(D) rac-(Z)-5-Fluoro-2-methyl-(4-pyridinylidene)-3-(N-benzyl)-indenyl-α-hydroxyacetamide is obtained from rac-5-fluoro-2-methyl-3-(N-benzyl)-α-hydroxyindenylacetamide using the procedure of Example 1, Part G ($R_1$=F, $R_2$=$CH_3$, $R_3$=OH, $R_4$=H, $R_5$=H, $R_6$=H, $R_7$=H, n=1, m=1, Y=4-pyridinyl).

EXAMPLE 32

2-[(Z)-5-Fluoro-2-Methyl-(4-Pyridinylidene)-3-(N-Benzyl)-Indenyl]-Oxyacetamide

For Pfitzner-Moffatt oxidation, a solution of rac-(Z)-5-fluoro-2-methyl-(4-pyridinylidene)-3-(N-benzyl)-indenyl-α-hydroxyacetamide (1 mmol) in DMSO (5 ml) is treated with dicyclohexylcarbodiimide (3 mmol). The mixture is stirred overnight, and the solvent is evaporated. The crude product is purified by flash chromatography to give the title compound ($R_1$=F, $R_2$=$CH_3$, $R_3$ and $R_4$ together form C=O, $R_5$=H, $R_6$=H, $R_7$=H, n=1, m=1, and Y=4-pyridinyl).

EXAMPLE 33 rac-(Z)-5-Fluoro-2-Methyl-(4-Pyridinylidene-3-(N-Benzyl)-Indenyl-α-(2-Propylamino)-Acetamide (A) 5-Fluoro-2-methyl-3-(N-2-propyl-N-hydroxy)-indenylacetamide is obtained from 5-fluoro-2-methylindenyl-3-acetyl chloride (Example 1, Step E) using the procedure of Example 31, Part A and replacing N-benzylhydroxylamine hydrochloride with N-2-propyl hydroxylamine hydrochloride.

(B) 5-Fluoro-2-methyl-3-(N-2propyl-N-mesyloxy)-indenylacetamide is obtained according to the procedure of Example 31, Part B.

(C) rac-5-Fluoro-2-methyl-3-(N-benzyl)-α-(2-propylamino)-acetamide. To 5-fluoro-2-methyl-3-(N-2-propyl-N-mesyloxy)-indenylacetamide (2 mmol) in $CH_2Cl_2$ (25 ml) at 0° C. is added benzylamine (4.4 mmol) in $CH_2Cl_2$ (15 ml) over a period of 30 minutes. The resulting solution is stirred at 0° C. for 1 hour, and at room temperature overnight. The solvent is removed, and the residue is treated with 1 N NaOH, and is extracted with $CH_2Cl_2$ (100 ml). The extract is washed with water (2×10 ml), and is dried over $MgSO_4$. After rotary evaporation, the product is purified by flash chromatography.

(D) rac-(Z)-5-Fluoro-2-methyl-(4-pyridinylidene)-3-(N-benzyl)-indenyl-α-(2-propylamino)-acetamide is obtained from rac-5-fluoro-2-methyl-3-(N-benzyl)-α-(2-propylamino)-acetamide using the procedure of Example 1, Part G ($R_1$=F, $R_2$=$CH_3$, $R_3$=isopropylamino, $R_4$=H, $R_5$=H, $R_6$=H, $R_7$=H, n=1, m=1, Y=4-pyridinyl).

EXAMPLE 34

(Z)-6-Methoxy-2-Methyl-(4-Pyridinylidene)-3 -(N-Benzyl)-Indenylacetamide (A) Ethyl-2-Hydroxy-2-(p-Methoxyphenyl)-1-Methylpropionate In a 500 ml. 3-necked flask is placed 36.2 g. (0.55 mole) of zinc dust, a 250 ml. addition funnel is charged with a solution of 80 ml. anhydrous benzene, 20 ml. of anhydrous ether, 80 g. (0.58 mole) of p-anisaldehyde and 98 g. (0.55 mole) of ethyl-2-bromoproplonate. About 10 ml. of the solution is added to the zinc dust with vigorous stirring, and the mixture is warmed gently until an exothermic reaction commences. The remainder is added dropwise at such a rate that the reaction mixture continues to reflux smoothly (ca. 30–35 min.). After addition is completed the mixture is placed in a water bath and refluxed for 30 minutes. After cooling to 0°, 250 ml. of 10% sulfuric acid is added with vigorous stirring. The benzene layer is extracted twice with 50 ml. portions of 5% sulfuric acid and washed twice with 50 ml. portions of water. The combined aqueous acidic layers are extracted with 2×50 ml. ether. The combined etheral and benzene extracts are dried over sodium sulfate. Evaporation of solvent and fractionation of the residue through a 6" Vigreux column affords 89 g. (60%) of the product, ethyl-2-hydroxy-2-(p-methoxyphenyl)-1-methylpropionate, B.P. 165–160° (1.5 mm.).

(B) 6-Methoxy-2-methylindanone

By the method described in Vander Zanden, Rec. Trav. Chim., 68, 413 (1949), the compound from part A is converted to 6-methoxy-2-methylindanone.

Alternatively, the same compound can be obtained by adding α-methyl-β-(p-methoxylphenyl)propionic acid (15 g.) to 170 g. of polyphosphoric acid at 50° and heating the mixture at 83–90° for two hours. The syrup is poured into iced water. The mixture is stirred for one-half hour, and is extracted with ether (3×). The etheral solution is washed with water (2×) and 5% $NaHCO_3$ (5×) until all acidic material has been removed, and is dried over sodium sulfate. Evaporation of the solution gives 9.1 g. of the indanone as a pale yellow oil.

(C) (Z)-6-Methoxy-2-methyl-(4-pyridinylidene,-3-(N-benzyl)-indenylacetamide

In accordance with the procedures described in Example 1, parts D–G, this compound is obtained substituting 6-methoxy-2-methylindanone for 6-fluoro-2-methylindanone in part D of Example 1.

EXAMPLE 35

(Z)-5-Methoxy-2-Methyl-(4-Pyridinylidene)-3 -(N-Benzyl)-Indenylacetamide (A) Ethyl 5-Methoxy-2-Methyl-3-Indenyl Acetate A solution of 3.4 g of 6-methoxy-2-methylindanone and 21 g. of ethyl bromoacetate in 45 ml. benzene is added over a period of five minutes to 21 g. of zinc amalgam (prepared according to Org. Syn. Coll. Vol. 3) in 110 ml. benzene and 40 ml. dry ether. A few cyrstals of iodine are added to start the reaction, and the reaction mixture is maintained at reflux temperature (ca. 65°) with external heating. At three-hour intervals, two batches of 10 g. zinc amalgam and 10 g. bromoester are added and the mixture is then refluxed for 8 hours. After addition of 30 ml. of ethanol and 150 ml. of acetic acid, the mixture is poured into 700 ml. of 50% aqueous acetic acid. The organic layer is separated, and the aqueous layer is extracted twice with ether. The combined organic layers are washed thoroughly with water, ammonium hydroxide and water. Drying over sodium sulfate, evaporation of solvent in vacuo followed by pumping at 80° (bath temperature)(1–2 mm.) gives crude ethyl-(1-hydroxy-2-methyl-6-methoxy-indenyl) acetate (ca. 18 g.).

A mixture of the above crude hydroxyester, 20 g. of p-toluenesulfonic acid monohydrate and 20 g. of anhydrous calcium chloride in 250 ml. toluene is refluxed overnight. The solution is filtered, and the solid residue is washed with toluene. The combined toluene solution is washed with water, sodium bicarbonate, water and then dried over sodium sulfate. After evaporation, the crude ethyl 5-methoxy-2-methyl-3-indenyl acetate is chromatographed on acid-washed alumina and the product is eluted with petroleum ether-ether (v./v. 50-100%) as a yellow oil (11.8 g., 70%).

(B) (Z)-5-Methoxy-2-methyl-(4-pyridinylidene)-3-(N-benzyl)-indenylacetamide

In accordance with the procedures described in Example 1, parts E–G, this compound is obtained substituting ethyl-5-methoxy-2-methyl-3-indenyl acetate for 5-fluoro-2-methindenyl-3-acetic acid in Example 1, part E.

EXAMPLE 36

(Z)-α-5-Methoxy-2-Methyl-(4-Pyridinylidene)-3-(N-Benzyl)-Indenylpropionamide (A) α-(5-Methoxy-2-methyl-3-indenyl)propionic acid The procedure of Example 35, part (A) is followed using ethyl α-bromopropionate in equivalent quantities in place of ethyl bromoacetate used therein. There is obtained ethyl α-(1-hydroxy-6-methoxy-2-methyl-1-indanyl)propionate, which is dehydrated to ethyl α-(5-methoxy-2-methyl-3-indenyl)propionate in the same manner.

The above ester is saponified to give α-(5-methoxy-2-methyl-3-indenyl)propionic acid.

(B) (Z)-α-5-Methoxy-2-methyl-(4-pyridinyl)-3-(N-benzyl)-a-methyl indenylpropionamide In accordance with the procedures described in Example 1, parts E–G, this compound is obtained substituting a-5-methoxy-2-methyl-3-indenyl)propionic acid for 5-fluoro-2-methylindenyl-3-acetic acid in Example 1, part E.

EXAMPLE 37

(Z) α-Fluoro-5 -Methoxy-2-Methyl-(4-Pyridinylidene)-3-(N-benzyl)-α-Indenylaceamide (A) Methyl-5-Methoxy-2-Methyl-3-Indenyl-α-Fluoro Acetate A mixture of potassium fluoride (0.1 mole) and methyl-5-methoxy-2-methyl-3-indenyl-α-tosyloxy acetate (0.05 mole) in 200 ml. dimethylformamide is heated under nitrogen at the reflux temperature for 2–4 hours. The reaction mixture is cooled, poured into iced water and then extracted with ether. The ethereal solution is washed with water, sodium bicarbonate and dried over sodium sulfate. Evaporation of the solvent and chromatography of the residue on an acid-washed alumina column (300 g.) using ether-petroleum ether (v./v. 20–50%) as eluent give the product, methyl-5-methoxy-2-methyl-3-indenyl-α-fluoroacetate.

(B) (Z) α-Fluoro-5-methoxy-2-methyl-(4-pyridinylidene)-3-(N-benzyl)indenylacetamide In accordance with the procedures described in Example 1, parts E–G, this compound is obtained substituting methyl-5-methoxy-2-methyl-3-indenyl-α-fluoroacetate for 5-fluoro-2-methylindenyl-3-acetic acid in Example 1, part E.

For the introduction of the =CH—Y part in Scheme III, any of the appropriate heterocyclic aldehydes may be used either directly in the base-catalyzed condensation or in a Wittig reaction in an alternative route. The aldehydes that may be used are listed in Table 1 below:

TABLE 1 pyrrol-2-aldehyde*
pyrimidine-2-aldehyde
6-methylpyridine-2-aldehyde*
1-methylbenzimidazole-2-aldehyde
isoquinoline-4-aldehyde
4-pyridinecarboxaldehyde*
3-pyridinecarboxaldehyde*
2-pyridinecarboxaldehyde*
4,6-dimethyl-2-pyridinecarboxaldehyde*

TABLE 1-continued 4-methyl-pyridinecarboxaldehyde*
4-quinolinecarboxaldehyde*
3-quinolinecarboxaldehyde*
2-quinolinecarboxaldehyde*
2-chloro-3-quinolinecarboxaldehyde*
pyrazinealdehyde
(Prepared as described by Rutner et al., JOC 1963, 28, 1898–99)
pyridazine-3-aldehyde
(Prepared as described by Heinisch et al., Monatshefte Fuer Chemie 108, 213–224, 1977)
pyrimidine-4-aldehyde
(Prepared as described by Bredereck et al., Chem. Ber. 1964, 97, 3407–17)
2-methyl-pyrimidine-4-aldehyde
(Prepared as described by Bredereck et al., Chem. Ber. 1964, 97, 3407–17) pyridazine-4-aldehyde
(Prepared as described by Heinisch et al., Monatshefte Fuer Chemie 104, 1372–1382 (1973))
1-methylindole-3-carboxaldehyde*
1-acetyl-3-indolecarboxaldehyde*

*Available from Aldrich

The aldehydes above can be used in the reaction schemes above in combination with various appropriate amines to produce compounds with the scope of this invention. Examples of appropriate amines are those listed in Table 2 below:

TABLE 2 benzylamine
2,4-dimethoxybenzylamine
2-methoxybenzylamine
2-fluorobenzylamine
4-dimethylaminobenzylamine
4-sulfonaminobenzylamine
1-phenylethylamine (R-enantiomer)
2-amino-2-phenylethanol (S-enantiomer)
2-phenylglycinonitrile (S-enantiomer)

EXAMPLE 38

(Z)-5-Fluoro-2-Methyl-(4-Pyridylidene)-3-(N-Benzyl) Indenylacetamide Hydrochloride (Z)-5-Fluoro-2-methyl-(4-pyridylidene)-3-(N-benzyl) indenylacetamide (1396 g; MW 384.45; 3.63 mol) from Example 1 is dissolved at 45° C. in ethanol (28 L). Aqueous HCl (12 M; 363 mL) is added stepwise. The reaction mixture is heated under reflux for 1 hour, is allowed to cool to room temperature, then stored at −10° C. for 3 hours. The resulting solid is filtered off, is washed with ether (2×1.5 L) and is air-dried overnight. Drying under vacuum at 70° C. for 3 days gives (Z)-5-fluoro-2-methyl-(4-pyridylidene)-3-(N-benzyl)indenylacetamide hydrochloride with a melting point of 207–209° C. ($R_1$=F, $R_2$=$CH_3$, $R_3$=H, $R_4$=H, $R_5$=H, $R_6$=H, $R_7$=H, n=1, m=1, Y=4-pyridinyl·hydrochloride). Yield: 1481 g (97%; 3.51 mol); MW: 420.91 g/mol.

$^1$H-NMR (DMSO-$d_6$): 2.18 (s,3,=C—$CH_3$); 3.54 (s,2, =$CH_2$CO); 4.28 (d,2,$NCH_2$); 6.71 (m,1,ar.); 7.17 (m,8,ar.); 8.11 (d,2,ar., AB system); 8.85 (m,1,NH); 8.95 (d,2,ar.,AB system); IR (KBr): 3432 NH; 1635 C=O; 1598 C=C.

BIOLOGICAL EFFECTS (A) Growth Inhibition

The compound of Example 1 was assayed for its growth inhibitory activity on the human colon carcinoma cell line, SW-480 obtained from ATCC (Rockville, Md.), to ascertain the degree of growth inhibition. Growth inhibition of this cell line is indicative of a benefit on precancerous lesions and neoplasms. The cell line and growth assay employed for such experiments are well characterized, and are used to evaluate the anti-neoplastic properties of NSAIDs. The assay is used by the United States National Cancer Institute in its screening program for new anti-cancer drugs.

Drug stock solutions were made in 100% DMSO and were then diluted with RPMI media for cell culture testing. All drug solutions were prepared fresh on the day of testing. The cultured cells were obtained at passage #99 and grown in RPM media supplemented with 5% fetal calf serum, and 2 mM glutamine, 100 U/ml penicillin, 100 U/ml streptomycin, and 0.25 µg/ml amphotericin. The cultures were maintained in a humidified atmosphere of 95% air and 5% $CO_2$ at 37° C. The cultures were passaged at preconfluent densities using a solution of 0.05% trypsin and 0.53 mM EDTA. Cells were plated at 1000 cells/well for 96 well flat-bottom microtiter plates.

Tumor cell growth inhibition was assessed using the Sulforhodamine B (SRB) protein binding assay. In this assay, tumor cells were plated in 96-well plates and treated with drug-containing media for six days (continuous exposure). For each plate, 6 wells were designated as no treatment controls, six wells as vehicle (0.1% DMSO) controls, and the remaining wells for drug dilutions with three wells per drug concentration. At the end of the exposure period, the cells were fixed and stained with sulforhodamine B, a protein binding dye. The dye was then solubilized, and the optical density of the resulting solution was determined on a 96-well plate reader. The mean dye intensity of the treated wells was then divided by the mean dye intensity in the control wells (6 wells of each) to determine the effect of the drug on the cells. Dye intensity is proportional to the number of cells or amount of protein per well. The resultant "percent inhibition" value then represents the degree of growth inhibition caused by the drug.

For each experiment, an $IC_{50}$ value was determined and used for comparative purposes. This value is equivalent to the concentration of drug needed to inhibit tumor cell growth by 50%. $IC_{50}$ value was obtained graphically by connecting the mean values for each drug concentration tested. Each experiment included at least three wells per drug concentration. Concentration was plotted on a log scale on the X-axis. $IC_{50}$ value obtained for the compound of Example 1 wa 0.724 for the SW-480 cell line.

(B) Cyclooxygenase (COX) Inhibition

COX catalyzes the formation of prostaglandins and thromboxane by the oxidative metabolism of arachidonic acid. The compound of Example 1 of this invention, as well as a positive control, (sulindac sulfide) were evaluated to determine whether they inhibited purified cyclooxygenase Type I (see Table 3 below).

The compounds of this invention were evaluated for inhibitory effects on purified COX. The COX was purified from ram seminal vesicles, as described by Boopathy, R. and Balasubramanian, J., 239:371–377, 1988. COX activity was assayed as described by Evans, A. T., et al., "Actions of Cannabis Constituents on Enzymes Of Arachidonate Metabolism Anti-Inflammatory Potential," Biochem. Pharmacol., 36:2035–2037, 1987. Briefly, purified COX was incubated with arachidonic acid (100 µM) for 2.0 min at 37° C. in the presence or absence of test compounds. The assay was terminated by the addition of TCA, and COX activity was determined by absorbance at 530 nm.

TABLE 3

| EXAMPLE | COX I<br>% Inhibition (100 µM) |
|---|---|
| | (* -1000 · M) |
| Sulindac sulfide | 86 |
| 1 | <25 |

(C) Apoptosis

Apoptosis was measured using an assay of cell death based on morphological characteristics of apoptotic cells (i.e., condensed chromatin). Drug preparation and cell culture conditions were the same as for the SRB assay described above, except that HT-29 human colon carcinoma cells were used. Confluent cultures were established in 12.5 cm² flasks by plating 0.5×10⁶ cells/flask. The cultures were assayed for apoptosis by fluorescent microscopy following labeling with acridine orange and ethidium bromide. Floating and attached cells were collected by trypsinization and washed three times in PBS. One ml aliquots were centrifuged (3 g). The pellet was resuspended in 25 µl media and 1 µl of a dye mixture containing 100 µg/ml acridine orange and 100 µg/ml ethidium bromide prepared in PBS and mixed gently. Ten µl of the mixture was placed on a microscope slide and covered with a 22 mm² coverslip, was examined with 40× dry objectives under epillumination by filter combination.

An observer blinded in regard to the identity of the samples scored at least 100 cells per sample. Apoptotic cells were identified by nuclear condensation of chromatin stained by the acridine orange or ethidium bromide. These results are provided in Table 4 below.

TABLE 4

Apoptosis Effects of Compounds

| EXAMPLE | Morphology<br>% Apoptotic Cells<br>(1 µM) | DNA Fragmentation | |
|---|---|---|---|
| | | FS (100 µM) | $EC_{50}$ (µM) |
| 1 | 88 | 4.2 | 29 |
| 2 | | 5.4 | |
| 3 | | 8.5 | |
| 4 | | 3.9 | |
| 38 | | | 15 |

Apoptosis was also measured based on the amount of fragmented DNA contained in cell lysates. Briefly, SW-480 colon adenocarcinoma cells were plated in 96-well microtitre plates ("MTP") at a density of 10K cells/well in 180 µl and were incubated for 24 hrs. Cells were then treated with 20 µl aliquots of appropriately diluted compound, and allowed to incubate for an additional 48 hrs.

After the incubation, samples were prepared according to the following steps. The MTP was centrifuged (15 min., 1000 rpm) and the supernatant was carefully removed by fast inversion of the MTP. The cell pellets in each well were resuspended in 200 µl lysis buffer and incubated for 45 min. at room temperature to lyse the cells. The lysates were then centrifuged (15 min., 1000 rpm) and 20 µl aliquots of the supernatant (=cytoplasmic fraction) were transferred into the streptavidin coated MTP for analysis. Care was taken not to shake the lysed pellets in the MTP (=cell nucleii containing high molecular weight, unfragmented DNA). Samples were analyzed immediately, because storage at 4C. or −20C. reduces the ELISA-signals.

Samples were then processed according to a DNA fragmentation assay protocol, and dose-response curves were generated based on optical density readings. Quantification of DNA was done by a commercially available photometric enzyme-immunoassay manufactured by Mannheim-Boehringer under the name "Cell Death Detection ELISA$^P$-$^{lus}$". The assay is based on a quantitative sandwich-enzyme-immunoassay-principle using mouse monoclonal antibodies directed against DNA and histones, respectively. This allows the specific determination of mono and oligonucleosomes in the cytoplasmatic fraction of cell lysates. In brief, the assay procedure is as follows. The sample (cell-lysate, serum, culture-supernatant etc.) is placed into a streptavidin-coated MTP. Subsequently, a mixture of anti-histone-biotin and anti-DNA-POD is followed by incubation for 2 hours. During the incubation period, the anti-histone antibody binds to the histone-component of the nucleosomes and simultaneously fixes the immunocomplex to the streptavidin-coated MTP via its biotinylation. Additionally, the anti-DNA-POD antibody reacts with the DNA component of the nucleosomes. After removal of unbound antibodies by a washing step, the amount of nucleosomes is quantified by the POD retained in the immunocomplex. POD is determined photometrically with ABTS® (2,2'-Azino-di[3-ethylbenzthiazolin-sulfonat])* as substrate.

Fold stimulation (FS=ODmax/ODveh), an indicator of apoptotic response, was determined for each compound tested. $EC_{50}$ values were determined either specifically by data analysis software, or by estimates based on the effective concentration range of each compound (ECR=min. effective dose-min. dose to peak effect). These FS and $EC_{50}$ values for the tested compounds are listed above in Table 4.

In addition, using the DNA fragmentation test above, a dose response for the compound of Example 1 was obtained. Those data are set forth in Table 5.

TABLE 5

| Dose (µM) | Apoptosis Level<br>(Mean OD Value ± SD) |
|---|---|
| 0.5 | 0.186 ± 0.008 |
| 1.0 | 0.207 ± 0.061 |
| 5.0 | 0.208 ± 0.073 |
| 10 | 0.296 ± 0.050 |
| 50 | 0.500 ± 0.048 |
| 100 | 0.633 ± 0.053 |
| 500 | 0.659 ± 0.012 |

The compounds of this invention can be formulated with pharmaceutically acceptable carriers into unit dosage forms in a conventional manner so that the patient in need of therapy for precancerous lesions can periodically (e.g., once or more per day) take a compound according to the methods of this invention. The exact initial dose of the compounds of this invention can be determined with reasonable experimentation One skilled in the art should understand that the initial dosage should be sufficient to achieve a blood plasma concentration approaching a percentage of the $IC_{50}$ value of the compound, with the percentage depending on the chemopreventative or chemotherapeutic indication. The initial dosage calculation would also take into consideration several factors, such as the formulation and mode of administration, e.g. oral or intravenous, of the particular compound. For example, assuming a patient with an average circulatory system volume of about four liters, based on the $IC_{50}$ values for compounds of this invention, one would calculate a dosage of about 0.6 mg–4.0 gr of such compounds for intravenous administration to achieve a systemic circulatory concentration equivalent to the $IC_{50}$ concentration.

Compounds of this invention are also cGMP-specific PDE inhibitors as taught in U.S. patent application Ser. No. 09/046,739 filed Mar. 24, 1998. Compounds can be tested for inhibitory effect on phosphodiesterase activity using either the enzyme isolated from any tumor cell line such as HT-29 or SW-480. Phosphodiesterase activity can be determined using methods known in the art, such as a method using radioactive $^3$H cyclic GMP (cGMP)(cyclic 3', 5'-guanosine monophosphate) as the substrate for PDE5 enzyme. (Thompson, W. J., Teraski, W. L., Epstein, P. M., Strada, S. J., *Advances in Cyclic Nucleotide Research,* 1:69–92, 1979, which is incorporated herein by reference). In brief, a solution of defined substrate $^3$H-cGMP specific activity (0.2 $\mu$M; 100,000 cpm; containing 40 mM Tris-HCl (pH 8.0), 5 mM MgCl$_2$ and 1 mg/ml BSA) is mixed with the drug to be tested in a total volume of 400 $\mu$l. The mixture is incubated at 30° C. for 10 minutes with partially purified cGMP-specific PDE isolated from HT-29 cells. Reactions are terminated, for example, by boiling the reaction mixture for 75 seconds. After cooling on ice, 100 $\mu$l of 0.5 mg/ml snake venom (O. Hannah venom available from Sigma) is added and incubated for 10 min at 30° C. This reaction is then terminated by the addition of an alcohol, e.g. 1 ml of 100% methanol. Assay samples are applied to a anion chromatography column ( 1 ml Dowex, from Aldrich) and washed with 1 ml of 100% methanol. The amount of radioactivity in the breakthrough and the wash from the columns in then measured with a scintillation counter. The degree of PDE5 inhibition is determined by calculating the amount of radioactivity in drug-treated reactions and comparing against a control sample (a reaction mixture lacking the tested compound).

Using such protocols, the cGMP-specific PDE inhibitor of Example 1 had an IC$_{50}$ value of 0.68 $\mu$M utilizing HT29 cell extracts.

It will be understood that various changes and modifications can be made in the details of procedure, formulation and use without departing from the spirit of the invention, especially as defined in the following claims.

We claim:

1. A method of inhibiting cGMP specific phosphodiesterase activity comprising exposing a cGMP-specific phosphodiesterase to compound of the formula:

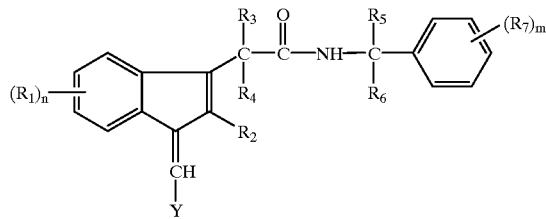

wherein R$_1$ is independently selected in each instance from the group consisting of hydrogen, halogen, lower alkyl, loweralkoxy, amino, loweralkylamino, di-loweralkylamino, loweralkylmercapto, loweralkyl sulfonyl, cyano, carboxamide, carboxylic acid, mercapto, sulfonic acid, xanthate and hydroxy;

R$_2$ is selected from the group consisting of hydrogen and lower alkyl;

R$_3$ is selected from the group consisting of hydrogen, halogen, amino, hydroxy, lower alkyl amino, and di-loweralkylamino;

R$_4$ is hydrogen, or R$_3$ and R$_4$ together are oxygen;

R$_5$ and R$_6$ are independently selected from the group consisting of hydrogen, lower alkyl, hydroxy-substituted lower alkyl, amino lower alkyl, lower alkylamino-lower alkyl, lower alkyl amino di-lower alkyl, lower alkyl nitrile, —CO$_2$H, —C(O)NH$_2$, and a C$_2$ to C$_6$ amino acid;

R$_7$ is independently selected in each instance from the group consisting of hydrogen, amino lower alkyl, lower alkoxy, lower alkyl, hydroxy, amino, lower alkyl amino, di-lower alkyl amino, amino lower alkyl, halogen, —CO$_2$H, —SO$_3$H, —SO$_2$NH$_2$, and —SO$_2$ (lower alkyl);

m and n are integers from 0 to 3 independently selected from one another;

Y is selected from the group consisting of quinolinyl, isoquinolinyl, pyridinyl, pyrinidinyl, pyrazinyl, imidazolyl, indolyl, benzimidazolyl, triazinyl, tetrazolyl, thiophenyl, furanyl, thiazolyl, pyrazolyl, or pyrrolyl, or subsituted variants thereof wherein the substituents are one or two selected from the group consisting of halogen, lower alkyl, lower alkoxy, amino, lower alkylamino, di-lower alkylamino, hydroxy, —SO$_2$(lower alkyl) and —SO$_2$NH$_2$; and pharmaceutically acceptable salts thereof.

2. The method of claim 1 wherein Y is selected from pyridinyl or quinolonyl.

3. The method of claim 1 wherein R$_1$ is selected from the group consisting of halogen, lower alkoxy, amino, hydroxy, lower alkylamino and di-loweralkylamino.

4. The method of claim 3 wherein R$_1$ is selected from the group consisting of halogen, lower alkoxy, amino and hydroxy.

5. The method of claim 1 wherein R$_2$ is lower alkyl.

6. The method of claim 4 wherein R$_2$ is lower alkyl.

7. The method of claim 1 wherein R$_3$ is selected from the group consisting of hydrogen, halogen, hydroxy, amino, lower alkylamino and di-loweralkylamino.

8. The method of claim 6 wherein R$_3$ is selected from the group consisting of hydrogen, halogen, hydroxy, amino, lower alkylamino and di-loweralkylamino.

9. The method of claim 7 wherein R$_3$ is selected from the group consisting of hydrogen, hydroxy and lower alkylamino.

10. The method of claim 8 wherein R$_3$ is selected from the group consisting of hydrogen, hydroxy and lower alkylamino.

11. The method of claim 1 wherein R$_5$ and R$_6$ are independently selected from the group consisting of hydrogen, hydroxy-substituted lower alkyl, amino lower alkyl, lower alkylamino-lower alkyl, lower alkyl amino di-lower alkyl, —CO$_2$H, —C(O)NH$_2$.

12. The method of claim 10 wherein R$_5$ and R$_6$ are independently selected from the group consisting of hydrogen, hydroxy-substituted lower alkyl, amino lower alkyl, lower alkylamino-lower alkyl, lower alkyl amino di-lower alkyl, —CO$_2$H, —C(O)NH$_2$.

13. The method of claim 1 wherein R$_5$ and R$_6$ are independently selected from the group consisting of hydrogen, hydroxy-substituted lower alkyl, lower alkyl amino di-lower alky, —CO$_2$H, —C(O)NH$_2$.

14. The method of claim 12 wherein R$_5$ and R$_6$ are independently selected from the group consisting of hydrogen, hydroxy-substituted lower alkyl, lower alkyl amino di-lower alkyl, —CO$_2$H, —C(O)NH$_2$.

15. The method of claim 1 wherein R$_7$ is independently selected in each instance from the group consisting of hydrogen, lower alkoxy, hydroxy, amino, lower alkyl amino, di-lower alkyl amino, halogen, —CO$_2$H, —SO$_3$H, —SO$_2$NH$_2$, amino lower alkyl, and —SO$_2$(lower alkyl).

16. The method of claim 14 wherein $R_7$ is independently selected in each instance from the group consisting of hydrogen, lower alkoxy, hydroxy, amino, lower alkyl amino, di-lower alkyl amino, halogen, —$CO_2H$, —$SO_3H$, —$SO_2NH_2$, amino lower alkyl, and —$SO_2$(lower alkyl).

17. The method of claim 1 wherein $R_7$ is independently selected in each instance from the group consisting of hydrogen, lower alkoxy, hydroxy, amino, halogen, —$CO_2H$, —$SO_3H$, —$SO_2NH_2$, amino lower alkyl ,and —$SO_2$(lower alkyl).

18. The method of claim 14 wherein $R_7$ is independently selected in each instance from the group consisting of hydrogen, lower alkoxy, hydroxy, amino, halogen, —$CO_2H$, —$SO_3H$, —$SO_2NH_2$, amino lower alkyl, and —$SO_2$(lower alkyl).

19. The method of claim 17 wherein at least one of the $R_7$ substituents is ortho- or para-located.

20. The method of claim 18 wherein at least one of the $R_7$ substituents is ortho- or para-located.

21. The method of claim 19 wherein at least one of the $R_7$ substituents is ortho-located.

22. The method of claim 20 wherein at least one of the $R_7$ substituents is ortho-located.

23. The method of claim 1 wherein Y is selected from the group consisting of quinolinyl, isoquinolinyl, pyridinyl, pyrimidinyl and pyrazinyl or said substituted variants thereof.

24. The method of claim 18 wherein Y is selected from the group consisting of quinolinyl, isoquinolinyl, pyridinyl, pyrimidinyl and pyrazinyl or said substituted variants thereof.

25. The method of claim 23 wherein the substituents of Y are one or two selected from the group consisting of lower alkoxy, amino, lower alkylamino, di-lower alkylamino, hydroxy, —$SO_2$(lower alkyl) and —$SO_2NH_2$.

26. The method of claim 24 wherein the substituents of Y are one or two selected from the group consisting of lower alkoxy, amino, lower alkylamino, di-lower alkylamino, hydroxy, —$SO_2$(lower alkyl) and —$SO_2NH_2$.

27. The method of claim 1 wherein said phosphodiesterase is PDE5.

28. (Z)-5-fluoro-2-methyl-(4-pyridylidene)-3-(N-benzyl) indenylacetamide hydrochloride.

* * * * *